(12) United States Patent
Salazar Altamar et al.

(10) Patent No.: US 9,433,584 B2
(45) Date of Patent: *Sep. 6, 2016

(54) APPARATUS AND PROCESS FOR ENCAPSULATING CAPSULES OR OTHER SOLID DOSAGE FORMS WITHIN CAPSULES

(71) Applicants: Carlos Salazar Altamar, Barranquilla (CO); Gustavo Anaya, Soledad (CO); Braulio Teran, Barranquilla (CO); Newman Aguas Navarro, Barranquilla (CO); Wilmer Herrera, Barranquilla (CO)

(72) Inventors: Carlos Salazar Altamar, Barranquilla (CO); Gustavo Anaya, Soledad (CO); Braulio Teran, Barranquilla (CO); Newman Aguas Navarro, Barranquilla (CO); Wilmer Herrera, Barranquilla (CO)

(73) Assignee: PROCAPS SA, Barranquilla (CO)

( * ) Notice: Subject to any disclaimer, the term of this patent is extended or adjusted under 35 U.S.C. 154(b) by 0 days.

This patent is subject to a terminal disclaimer.

(21) Appl. No.: 14/636,013

(22) Filed: Mar. 2, 2015

(65) Prior Publication Data
US 2015/0164814 A1 Jun. 18, 2015

Related U.S. Application Data

(63) Continuation of application No. 13/137,045, filed on Jul. 18, 2011, now Pat. No. 8,967,989.

(60) Provisional application No. 61/344,416, filed on Jul. 19, 2010.

(51) Int. Cl.
| | |
|---|---|
| *A61J 3/07* | (2006.01) |
| *A61K 9/48* | (2006.01) |
| *A61J 7/00* | (2006.01) |
| *A61K 31/60* | (2006.01) |
| *A61K 45/06* | (2006.01) |
| *B65D 83/04* | (2006.01) |

(52) U.S. Cl.
CPC ............... *A61K 9/4808* (2013.01); *A61J 3/07* (2013.01); *A61J 7/0076* (2013.01); *A61K 9/4833* (2013.01); *A61K 31/60* (2013.01); *A61K 45/06* (2013.01); *B65D 83/04* (2013.01)

(58) Field of Classification Search
None
See application file for complete search history.

*Primary Examiner* — H. Sarah Park
(74) *Attorney, Agent, or Firm* — Isaac Angres

(57) ABSTRACT

The present invention provides an apparatus and process for making softgel capsules having incorporated therein other solid dosage forms selected from the group consisting of pellets, smaller capsules, smaller tablets, sustained release solid dosage forms, immediate release solid dosage forms, extended release solid dosage forms and zero order release solid dosage forms, said apparatus comprising: (a) two spreader boxes; (b) two casting drums; (c) a pair of rotary dies having means for suction; (d) a liquid fill system; (e) a wedge for heating gelatine ribbons and feeding said fill; and (f) two lateral dispensing devices said lateral dispensing devices including hoppers having said solid dosage forms, channelguides for transporting said solid dosage forms and a grasping claw for dispensing said solid dosage form into the softgel pocket formed in the rotary dies.

3 Claims, 6 Drawing Sheets

APPARATUS AND PROCESS FOR ENCAPSULATING CAPSULES OR OTHER SOLID DOSAGE FORMS WITHIN CAPSULES

This application is a continuation of US application Ser. No. 13/137,045 filed Jul. 18, 2011; now U.S. Pat. No. 8,967,989 issued Mar. 3, 2015, the entire contents of which are incorporated by reference. This application also claims the priority benefit under 35 U.S.C. section 119 of U.S. Provisional Patent Application No. 61/344,416 entitled "Apparatus And Process For Encapsulating Capsules Within Capsules" filed Jul. 19, 2010, which is in its entirety herein incorporated by reference.

FIELD OF THE INVENTION

This invention relates to methods and apparatus for the production of soft gelatin capsules containing internally other solid dosage forms or smaller capsules within said capsules. The capsules of the invention are now well established as a means for providing a variety of liquid products such as drugs and dietary supplements in a readily ingestible form especially when two drugs are not compatible with each other.

This invention further relates to softgels (or soft gelatin capsules) containing one or more smaller capsules within such capsules and to a process and apparatus for the manufacture thereof. The present invention also relates to a gelatin capsule of the soft type containing multiple active ingredients or the like, and more particularly to a novel gelatin capsule capable of containing multiple medicines or dietary supplement as the content separated from each other, and its manufacturing method and manufacturing apparatus.

The present invention also relates generally to a method and apparatus for forming capsules within capsules containing a measured amount of not compatible medicinals and more particularly to a method and apparatus for forming capsules. The method and apparatus of the present invention are particularly useful in connection with forming softgel capsules having other solid dosage forms containing multiple pharmaceutical product, such as for example medicines, vitamins, food supplements and the like which are not compatible with each other.

The present invention further relates to encapsulation machines and, more particularly, to soft encapsulation machines which make soft gelatin capsules having other smaller capsules within or other solid dosage form.

The invention is particularly useful for making formulations wherein two active ingredients are not compatible with each other but it is desirable to administer them in the same dosage form i.e., a capsule within a capsule or another solid dosage form within a capsule.

BACKGROUND OF THE INVENTION AND DESCRIPTION OF THE PRIOR ART

The art of encapsulation has been known for many years, particularly for the production of unit dosage forms containing various pharmaceutical products. Normally, such pharmaceutical capsules are composed of gelatin or some modification thereof, which is fabricated essentially into two different forms, namely, the so-called hard gelatin capsule and the soft gelatin capsule.

It is also known that conventional soft gelatin capsules are a preferred from of administration for medicaments and similar products; especially liquids, pastes, solids dispersed in liquids, or dry solids. Soft gelatin capsules also possess particular advantages for substances which require total protection from air and light, because the gelatin is completely sealed around the contents. An important example is for the encapsulation of vitamins, which has resulted in a high degree of stability thereof.

Hard gelatin capsules are also known in the art, and are generally formed from two distinct parts, namely the "cap" and the "body", fitting one into the other so as to form the complete capsule. The cap and the body are manufactured by the same process consisting of immersing in a gelatin solution the end of a mandrel whose form corresponds to the inner volume of the cap or of the body, then withdrawing the mandrel from the solution and letting the layer of gelatin thus deposited dry, which is then removed like a glove finger. Hard shell capsules so formed have problems of leakage and do not provide adequate protection from air and light Soft gelatin capsules, now more commonly known as softgels, have been well known and widely used for many years. Softgels generally comprise an outer shell primarily made of gelatin, a plasticizer, and water, and a fill contained within the shell. The fill may be selected from any of a wide variety of substances that are compatible with the gelatin shell. Softgels are widely used in the pharmaceutical industry as an oral dosage form containing many different types of pharmaceutical and vitamin products. In addition to use as an oral dosage form for drugs and vitamins, soft gelatin capsules or softgels are also designed for use as suppositories for rectal or vaginal use. Other uses are for topical and ophthalmic preparations and the like. The cosmetic industry also uses softgels as a specialized package for various types of perfumes, oils, shampoos, skin creams and the like. Softgels are available in a great variety of sizes and shapes, including round shapes, oval shapes, oblong shapes, tube shapes and other special types of shapes such as stars. The finished capsules or softgels can be made in a variety of colors. Also, opacifiers may be added to the shell.

The process for making softgel capsules includes the step wherein the gelatin shell and the fill material come together to form Softgel capsules. It takes place in a closed environment called clean room where the relative humidity is around 20%. The gelatin shell and fill material are brought together simultaneously in the encapsulation machine.

The process is basically performed as follows: a pump delivers the warm gelatin over two chilled drums which are located at both opposite sides of the machine, through a spreader box that sits over each drum. The warm liquid gelatin flows over the drums and this transforms the liquid gelatin into two solid ribbons of gel. The left and right ribbons pass over rollers which feed them through two die rolls. These die rolls determine the shape and size of softgels and cut the Softgel shell from the ribbons as they turn around.

Simultaneously, a sensitive and high accuracy positive displacement pump delivers the fill material into a heated wedge which sits between rotary dies. This wedge injects the fill material into the die cavities between ribbons just right before the die rolls cut the ribbons and seal the two halves together. Warm just formed softgels slide gently through a chute onto a conveyor belt which carries them to the tumble dryer where cooling and drying process takes place.

In more specific detail, typical soft encapsulation machines form at least two flexible gelatin sheets or ribbons by cooling molten gelatin on separate drums then lubricating and guiding the sheets into communication with each other over co-acting dies while simultaneously dispensing a desired quantity of fill material between the sheets in synch with cavities in the outer surfaces of the dies to produce soft capsules. The encapsulation machines typically utilize gearing to control the relative rotations of the various components and fill mechanisms to synchronize the operation of these various components. The synchronization of these various components, however, can vary depending upon a variety of factors, such as the particular dies used, the number of cavities and the size of the cavities on the dies, and the type of material used to form the sheets. To change the synchronization of the various components, mechanical gears are required to be changed to obtain the desired ratios and synchronization of these components. The changing of gears, however, is time intensive. Additionally, the use of mechanical gears provides finite gear ratios which limit the synchronization of the various components to the mechanical gears that are available. Thus, it would be advantageous to provide a capsule machine wherein the synchronization and rates at which the various components operate can be altered without the necessity of changing gears. Additionally, it would be advantageous if the synchronization between the various components can be infinite to thereby allow more precise synchronization between the various components. It would also be advantageous to allow various components, such as the fill mechanism, to be adjusted independently of the other components while the machine is running to allow for adjustments of the timing of fill material inserted into each of the soft capsules. It would also be advantageous to eliminate the use of casting drums in the making of softgel capsules.

During the operation of the capsule making machine, the contact between the adjacent dies can be adjusted by the operator of the capsule making machine. Typically, the operator is able to move one of the dies closer to the other die so that the pressure or force exerted on the sheets passing between the adjacent dies can be adjusted. Such adjustments, typically are mechanical adjustments made by fluid actuators, such as pneumatic cylinders. The operator is able to adjust the pneumatic pressure thereby altering the force the dies exert on one another and on the sheets. This adjustability allows an operator to customize the pressure to ensure that quality soft capsules are produced. However, the dies are susceptible to premature failure and/or wear when the pressure or force between the two dies is more than that required to produce acceptable soft capsules. Thus, it would be advantageous to monitor/record the pressure applied to the dies so that quality capsules are produced without inducing excessive wear or premature wear on the dies.

A material fill mechanism is used to supply the fill material that is encapsulated within the soft capsules. When the fill material is a liquid, such as a liquid medication or die for a paint ball capsule, the fill mechanism includes a plurality of positive displacement plunger-type pumps that are arranged in a housing above the dies. The plunger-type pumps are positioned on a yoke that moves linearly in a reciprocating motion to allow the plunger-type pump to fill with the liquid fill material on one stroke and subsequently discharge the liquid fill material on the other stroke. A valving arrangement between opposing pumps is utilized to control the discharge and filling of the pumps. The valve arrangement includes a sliding member that moves linearly back and forth in a direction generally perpendicular to the linear motion of the yoke. The discharge of the liquid fill material into the sheets as they are passing through the dies is coordinated with the operation of the dies to insure that the timing of the injection of the liquid fill material is synchronized with the cavities on the dies. Typically, this synchronization has been performed through the use of mechanical gears that link the timing of the stroke to the rotation of the dies. Thus, in order to adjust the synchronization a mechanical gear change is required which is time consuming. Additionally, the timing is limited to a finite number of gear ratios as determined by the gears that are available.

The sliding member of the valving mechanism requires lubrication. Typically, the lubrication is provided by a lubricating pump with its own separate drive. However, the use of a separate drive to operate the lubricating pump adds additional complexity and components to the capsule machine. Thus, it would be advantageous if a motion of the slide member and/or the yoke could be utilized to drive the lubrication pump.

The pumps are typically contained within a housing that is filled with a lubricating oil that is used to lubricate the sliding member. The pumps, however, can leak around their seals and contaminate the lubricating oil with the leaking fill material. Contamination of the oil requires a time consuming and possibly difficult clean up and can cause the lubricating oil to not perform as designed thereby increasing the wear on the sliding surfaces and decreasing the life span of the sliding surfaces. Thus, it would be advantageous to capture any fill material that leaks from the pumps and deter or prevent the liquid fill material from contaminating the lubricating oil within the pump housing.

The pumps are typically driven by a drive mechanism that is also located within the pump housing. Because the drive mechanism is located in the pump housing, it is possible for liquid fill material that leaks from the pumps to contaminate not only the lubrication oil but also the drive mechanism. When switching from one fill material to another, the pump and all of the components in the pump housing are required to be thoroughly cleaned to remove all contamination. The locating of the drive mechanism within the pump housing provides additional components that must also be cleaned when changing the fill material. Thus, it would be advantageous to separate the drive mechanism from the pump housing to reduce the components that are required to be cleaned when changing fill material.

The soft capsules produced by the encapsulation machine are transported from the encapsulation machine to a dryer to additionally dry the soft capsules and to make them into final form. The soft capsules are transported from the encapsulation machine to the dryer by a conveyor that extends along the front of the encapsulation machine. The conveyor can be contaminated by the fill material during operation of the encapsulation machine. When it is desired to switch the product being produced on the encapsulation machine, the conveyor must be removed from the encapsulation machine and cleaned to remove any contaminates thereon. The conveyor is driven by a motor that is attached to the conveyor. When it is necessary to remove the conveyor for cleaning, the motor must also be taken with the conveyor which makes it more difficult to remove and transport the conveyor and requires additional time to disconnect the motor from the encapsulation machine. The present invention provides an encapsulation machine that overcomes the above-described disadvantages of typical encapsulation machines.

Applicant is aware of the following publications briefly discussed below. U.S. Pat. No. 1,970,396 features a method and machine for producing soft gelatin capsules in an automated process. The method involves the formation of two gelatin sheets or films through the use of a gravity fed spreader box, cooling the liquid gelatin on two separate webs, then lubricating and guiding the two sheets into communication with each other between two co-acting dies while simultaneously dispensing the proper amount of medicine or other filling material between the sheets in registration with half cavities in the outer surface of the dies.

U.S. Pat. No. 5,761,886 discloses an apparatus for forming capsules that provides rotary dies that are independently moveable and the ability to vary the speed of the dies during the formation of a single capsule. The '886 device also utilizes independently controlled casting drums to reduce "set-up" time and provide better quality control. Even though the '886 patent discloses a very sophisticated encapsulation machine, it still utilizes a gravity fed spreader box for formation of the encapsulating ribbon.

Other patents relating to encapsulation techniques which disclose the use of spreader boxes to create the film or ribbon on a casting drum include U.S. Pat. Nos. 2,288,327; 2,774,988; 5,246,638; 5,735,105; and 6,022,499.

SUMMARY OF THE INVENTION

Figure 1:
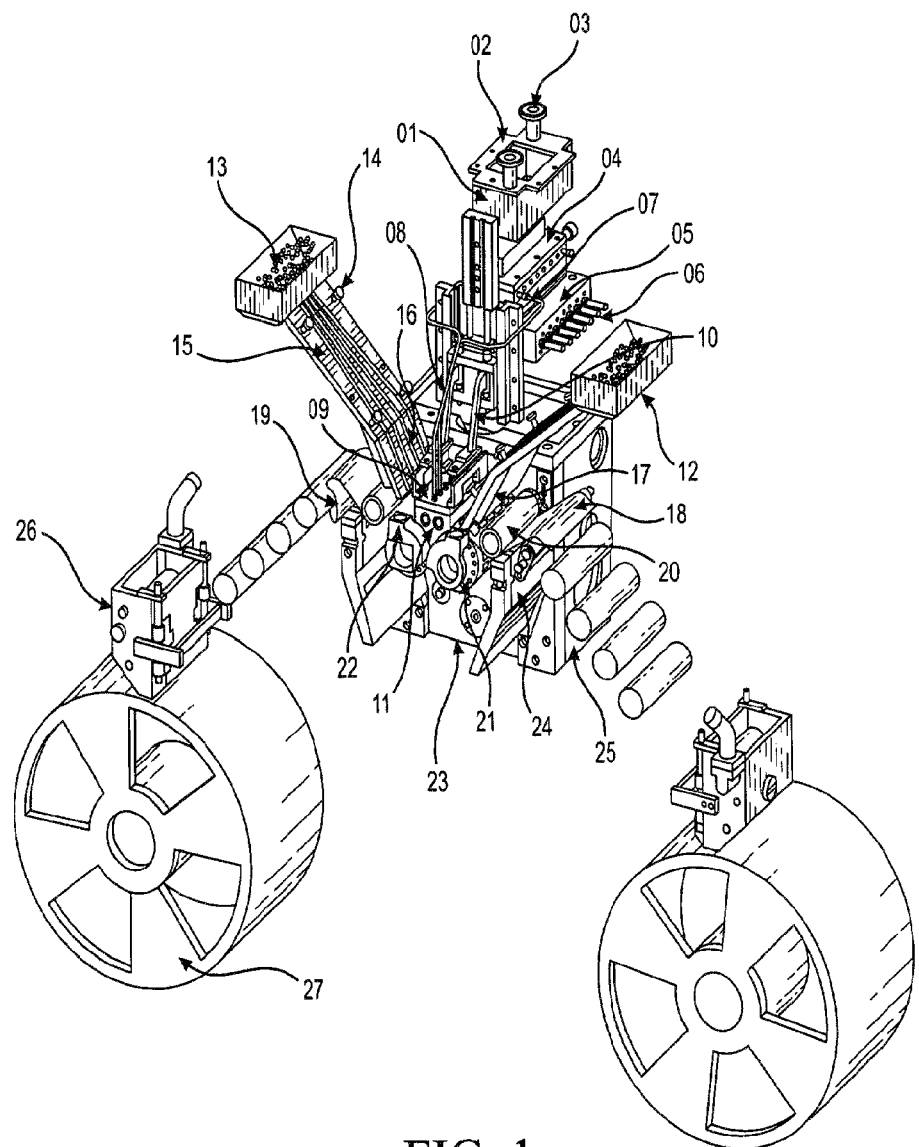
FIG. 1 is a front view of the complete apparatus of the invention showing all the elements of the apparatus.

The present invention responds specifically to the long-felt need heretofore unmet by the prior art, and especially with a view to overcoming the inherent inadequacies of combination of pharmaceuticals that are not compatible for oral delivery to mammals. The composition is a pharmaceutical combination i.e., a capsule within a capsule providing the convenience and reliability of oral administration, while providing near simultaneous delivery in vivo of incompatible substances. The composition is shelf stable when formulated.

The foregoing, and other advantages of the present invention, are realized in one aspect thereof in an oral pharmaceutical composition that is a combination of incompatible active ingredients. The composition comprises a double soft capsule which includes one pharmaceutical in a first capsule which is enclosed second soft capsule also containing a second active ingredient. The soft capsules are preferably made of gelatin. The active ingredients may be combined with acceptable grade carriers.

In another aspect, the invention is a method of simultaneously delivering incompatible compounds to mammals in vivo. Such delivery is achieved by administering orally to a mammal a double soft capsule containing a first substance in a first capsule, which is enclosed with a second substance, incompatible with the first substance, in a second larger soft capsule. In another embodiment, this invention provides a method for preparing shelf-stable compositions of incompatible substances, which includes the use of multiple capsules of variable composition. Such method is accomplished manually or by the apparatus of the invention further described below.

As used herein, the term "incompatible" is meant to refer to substances which deleteriously react with one another when combined in desired levels or concentrations.

The invention also provides an apparatus for making softgel capsules having incorporated therein other solid dosage forms selected from the group consisting of pellets, smaller capsules, smaller tablets, sustained release solid dosage forms, immediate release solid dosage forms, extended release solid dosage forms and zero order release solid dosage forms, said apparatus comprising: (a) two spreader boxes; (b) two casting drums; (c) a pair of rotary dies having means for suction; (d) a liquid fill system; (e) a wedge for heating gelatine ribbons and feeding said fill; and (f) two lateral dispensing devices said lateral dispensing devices including hoppers having said solid dosage forms, channelguides for transporting said solid dosage forms and a grasping claw for dispensing said solid dosage form into the softgel pocket formed in the rotary dies.

The invention further provides a dispensing device for dispensing and feeding solid dosage forms into a softgel capsule said dispensing and feeding device including a hopper having said solid dosage forms, channelguides for transporting said solid dosage forms and a grasping claw for dispensing said solid dosage form.

The instant invention also provides a method for making softgel capsules having incorporated therein other solid dosage forms, said method comprising: casting a gel forming composition to make films; (b) passing said films through a pair of rotary dies having vacuum means to make pockets; (c) feeding smaller solid dosage forms into said pockets using a lateral dispensing and feeding system that uses a grasping claw; (d) filling said pockets with a medicine formulation in liquid form via a wedge segment; and (e) forming said capsule by sealing the pockets together.

The invention is also a process for making a softgel capsule having incorporated therein another capsule, said process comprising: (a) feeding film sheets between a first die roll and a second die roll wherein each of the die rolls have capsule pockets in a plurality of rows and said capsule pockets have at least one orifice for application of suction; (b) applying suction while said film is in place in the capsule pockets; (c) feeding via guidechannels through a lateral dispensing device having a hopper and a grasping claw preformed smaller capsules onto the film sheets overlying the die rolls at positions having the capsule pockets; (d) filling said capsule pockets also via a wedge segment with a liquid medical formulation; and (e) cutting the film sheets about the capsule pockets to form said soft gel capsules having capsules in combination with a suitable liquid pharmaceutical combination.

The invention further provides softgel capsules incorporated into an outer softgel capsule, tablets incorporated into an outer softgel capsule, microgranules incorporated into an outer softgel capsule, and any combination between softgels, tablets and/or microgranules incorporated into an outer softgel capsule.

The instant invention also provides a softgel capsule having incorporated therein another solid dosage form selected from the group consisting: (a) one capsule contains an omega oil and the other solid dosage form is a capsule having a statin; (b) one capsule contains a non-steroidal antiinflammatory and the other solid dosage form contains and antihistamine; and (c) one capsule contains and omega oil and the other solid dosage form contains a salicylate.

Other advantages and a fuller appreciation of the specific adaptations, compositional variations, and physical and chemical attributes of the present invention will be gained upon an examination of the following detailed description of the invention, taken in conjunction with the accompanying drawings and appended claims.

DETAILED DESCRIPTION OF THE INVENTION

The present invention provides an innovative and efficient system for the manufacture of capsules with two or more internal components. Although the internal components may be incompatible the invention is also intended to provide internal components that are compatible but are intended to be released at different intervals.

The present invention provides an advanced drug delivery system that places different pharmaceuticals forms in a single dosage combination. The invention allows delivering incompatible pharmaceutical actives in the form of solid, liquid, microgranules, gels, hard shell or soft gel capsules within an outer softgel capsule.

The novel dosage system allows for combining different therapeutic entities that have never been combined before, via oral, ovules, or suppositories.

For the multi-drugs regimen patients and due to the incompatibility of some actives that can not be combined in a single dose, the instant invention offers a universe of possibilities for current and future new drugs combinations and supplies different releasing delivery.

In the present invention, existing and proven delivery systems are combined in a highly reliable, easy to use and affordable manufacture that give the resulting dosage form unique characteristics to deliver single or multiple APIs regardless of physical-chemical compatibility and/or stability liabilities.

For the multi-drugs regimen patients this delivery system is a viable alternative; due to the manufacturing of IR plus MR combinations in tablets and hard-gelatin capsules while enhancing dosing accuracy and by-passing dissolution barriers and coating issues. It allows the formulation of combination products, highly needed to assure patient compliance and allow synergic clinical effects in a safe and stable dosage form.

Some of the most important advantages are:
Fast and sustained release in a single dose.
Gastric or intestinal release in the same dose.
Fewer intakes to be administered.
Simplicity of regimen reduces mistakes.
Impossible to be falsified.
Reduces number of Rx's prescribed by Physician.
Smaller number of presentations to maintain.

The invention further provides soft-gelatin capsules as a immediate-release (IR) delivery system, that upon rupture, it releases immediate or modified release (MR) tablets, capsules, softgels, granules and/or microgranules. Compatible and/or incompatible pharmaceutical active ingredients, and/or blends of IR and MR dosage forms of the same or different active pharmaceutical ingredients (APIs) can be dosed simultaneously in a single capsule. These capsules may be designed to be administered orally, vaginally or rectally, as needed.

Referring in detail to the apparatus shown in FIG. 1, reference numeral 1 illustrates a medicine hopper having a cover 2 and a medicine feeder 3 connected with a clamp. The apparatus further includes a medicine distributor system 4, pump 5 to pump medicine and further includes plunger 6. The apparatus also includes a fitting distributor connection 7, medicine tubing/hoses 8, a segment coupling connection 9, a support segment 10, and wedge segment 11.

The apparatus has lateral hoppers 12 and 13 containing smaller capsules or other solid dosage forms that are intended to be encapsulated by the soft gels being formed in the rotary dies. The lateral hopper dispensing system includes acrylic or other material knob fasteners 14 and acrylic substrate 15 having guide channels/tracks 16 for the smaller capsules or other smaller solid dosage forms such pellets or minitablets, etc. The lateral dispensing system of the invention includes a grasping claw 17 for dispensing the smaller capsules coming through channels/track 16. The apparatus further includes the conventional aspects of making softgel capsules which includes a gelatin film 18, guiding rollers 19, tensioner 20, rotary mold 21, a vacuum system 22, capsule exit 23 after the capsule is formed, a yoke support arm 24, housing 25, spreader gel dispensing boxes and casting drum 27.

Figure 2:
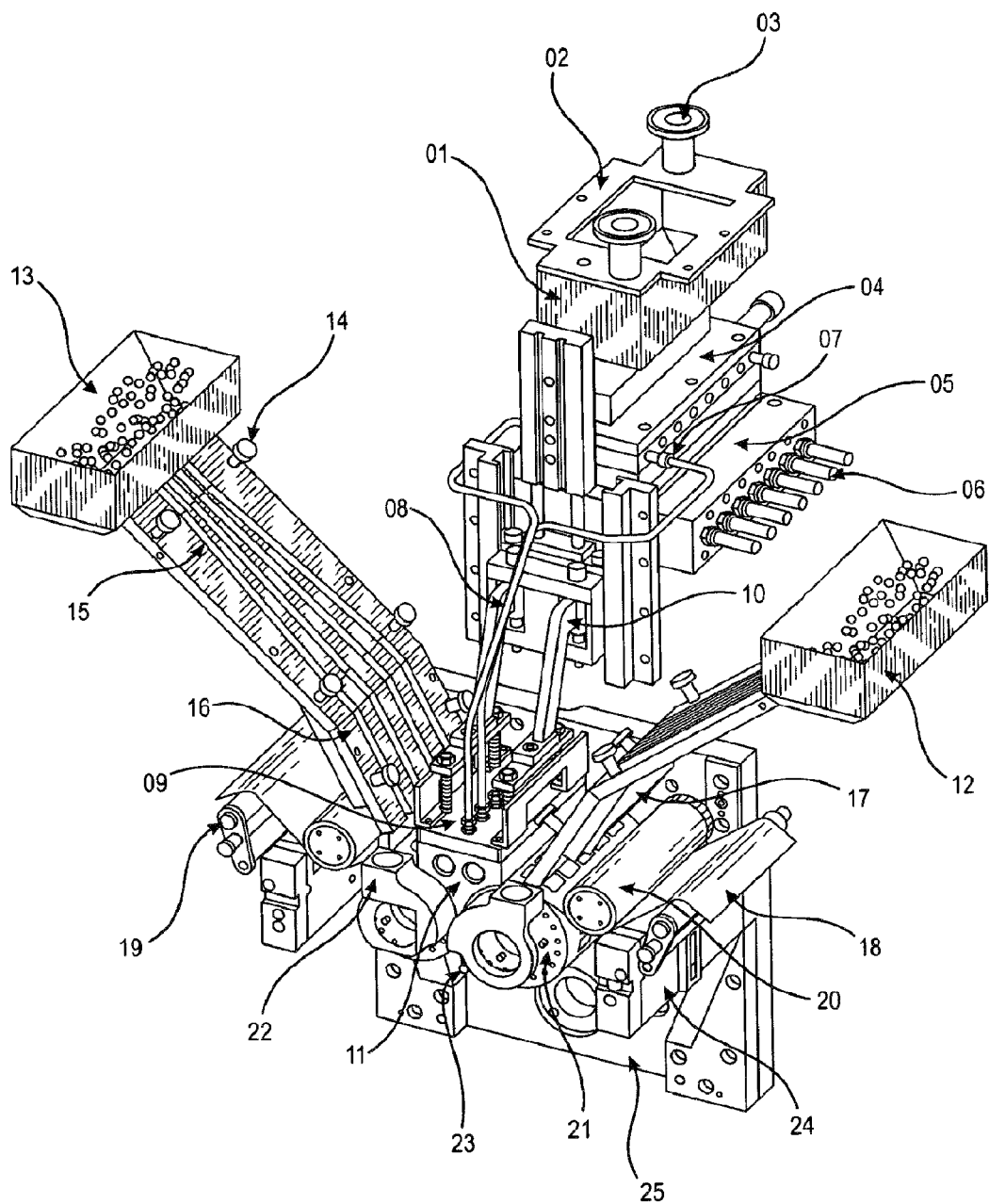
FIG. 2 is also a front view of the apparatus of FIG. 1 without the spreader boxes and casting drums.

FIG. 2 illustrates the apparatus of FIG. 1 without the spreader gel dispensing boxes and casting drums. The reference numerals in FIG. 2 are identical as those in FIG. 1.

The film-forming materials of the invention comprise at least one component selected from the group consisting of gelatin, starch, carrageenans, gums or synthetic materials such as hydroxypropyl-methylcellulose (HPMC), other hydroxyalkylated celluloses and the like. The film-forming material typically has an aqueous base and is considered to be ingestible. As used herein, the term "ingestible" is used to indicate a film-forming material that dissolves under conditions simulating the human digestion tract or water.

Figure 3:
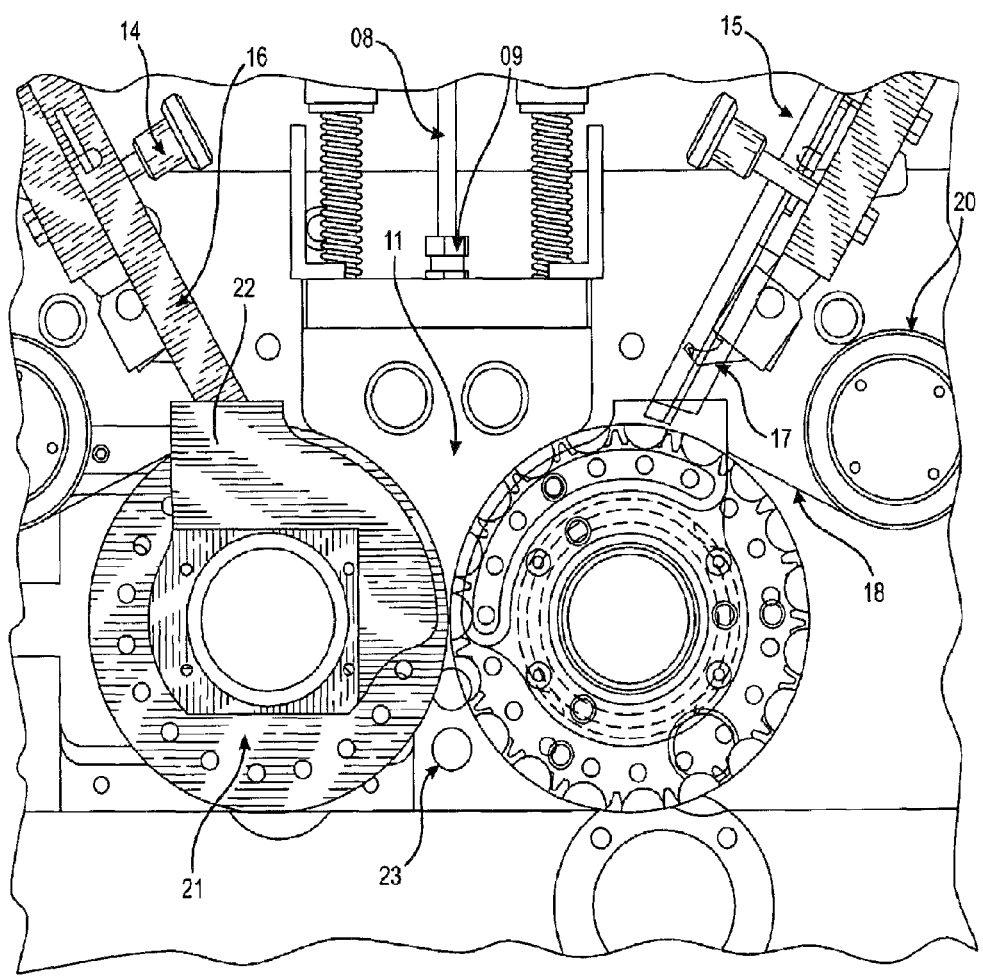
FIG. 3 is a front view of the mechanism for filling the capsules with other capsules.

FIG. 3 shows the dispensing and feeding of solid dosage forms or capsules that come from hoppers 12 and 13 (not shown-See FIGS. 1 and 2) controlled by grasping claw 17 with volume capacity for accurate dosing fixed within the capsule. The smaller dosage form or smaller capsules is fed through guide channels 16 and deposited inside a half pocket as the softgel capsule is being formed in rotary die 21. The grasping claw 17 releases each capsule into each packet as the rotary die moves. The final capsule is also filled with additional pharmaceutical actives in liquid form injection tubing 8. After filling the formed capsule 23 falls-through to a conveyor belt and then transported for drying.

Figure 4:
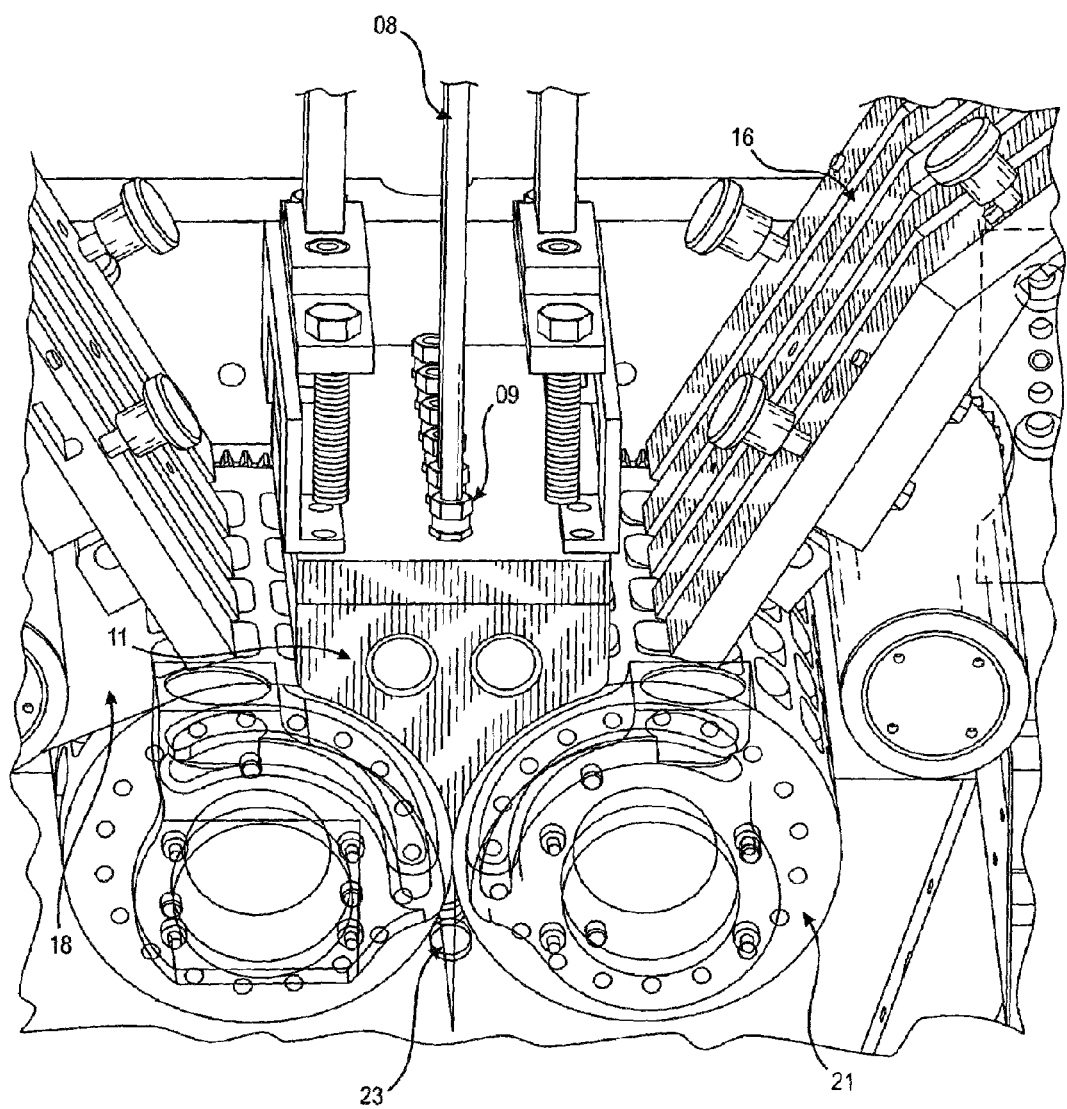
FIG. 4 is also a front view of how the smaller capsules are dispensed into the larger capsule.

FIG. 4 further illustrates in more details the feeding of solid dosage forms or capsules into the rotary molding process for making softgel capsules containing internally other dosage forms such as smaller capsules, pellets, small tablets, etc. The feeding of the internal capsule is made by an independent dispenser having guide channels 16 so that as capsules are deposited in the pocket of the rotary die/mold 21, the wedge segment 11 is used to simultaneously dispense a liquid medicine product to fill the capsule. As is well known gelatin film 18 is used to form the softgel pocket in the rotary die/mold 21.

Figure 5:
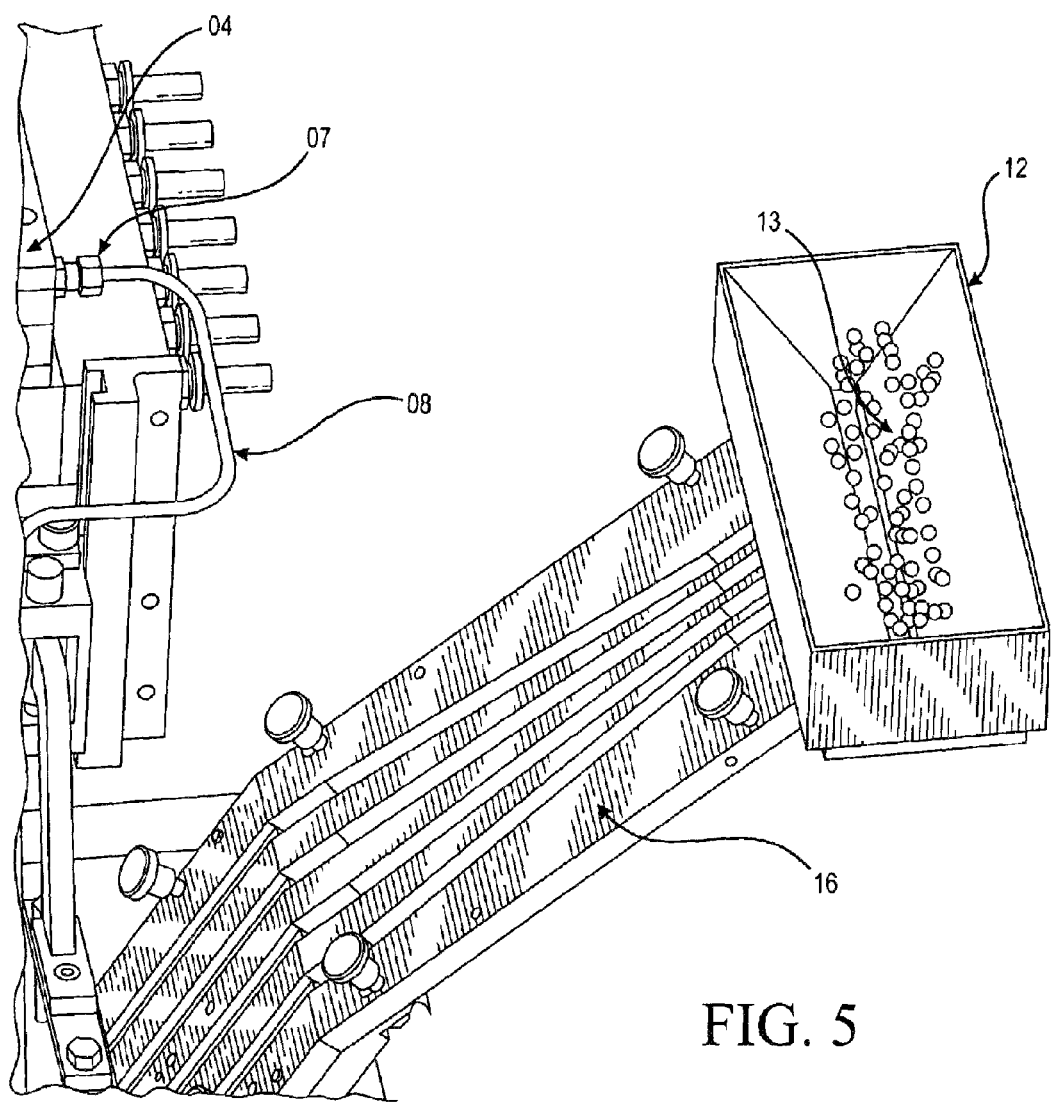
FIG. 5 shows the smaller capsule hopper having capsules which are fed via guiding channels into the larger capsule.

FIG. 5 shows one of the lateral hoppers having smaller solid dosage forms or smaller capsules to be filled inside another softgel capsule. The hopper 12 having capsules 13, are released from the hopper and deposited and guided through guidechannels 16 which in turn leads to the pocket in the rotary mold that is in a tangential position.

Figure 6:
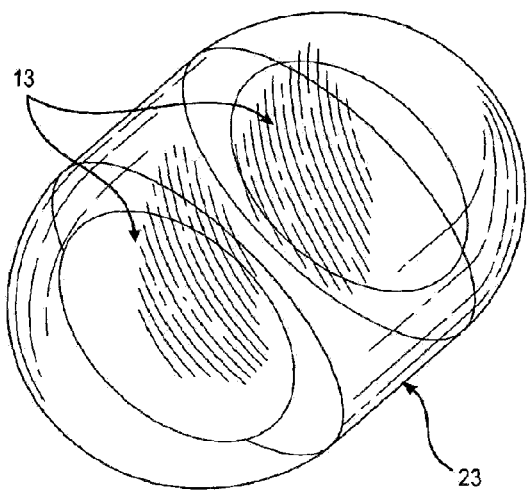
FIG. 6 shows a representative end product of the invention containing two capsules inside another capsule.
Figure 7:
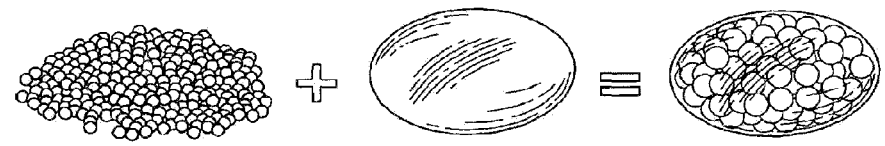
FIG. 7 are representative examples of products contemplated by the invention.
Figure 7:
Figure 7:

FIG. 6 illustrates a finished capsule of the invention. One or more smaller capsules may be encapsulated in any way into another immersed in a liquid or solution containing a pharmaceutical active ingredient.

The resulting products of the invention include softgel capsules having incorporated therein another solid dosage form selected from the group consisting of: (a) one capsule contains an omega oil and the other solid dosage form is a capsule having a statin; (b) one capsule contains a non-steroidal antiinflammatory and the other solid dosage form contains and antihistamine; and (c) one capsule contains and omega oil and the other solid dosage form contains a salicylate.

Typically the omega oil is an omega-3 oil and the statin is selected from the group consisting of mevastatin, lovastatin, pravastatin, fluvastatin, simvastatin, rosuvastatin, cerivastatin and atorvastatin and derivatives and analogs thereof.

The non-steroidal antiinflammatory acid is selected from the group consisting of ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucloxic acid, indomethacin, sulindac, tolmetin, zomepirac, diclofenac, fenclofenac, alclofenac, ibufenac, isoxepac, furofenac, tiopinac, zidometacin, acemetacin, fentiazac, clidanac, oxpinac, mefenamic acid, meclofenamic acid, flufenamic acid, niflumic acid and tolfenamic acid, diflunisal, flufenisal and piroxicam.

The antihistamine is selected from the group consisting of diphenhydramine, loratadine, cetirizine, fexofenadine, hydroxyzine, cyproheptadine, chlorphenamine, clemastine and desloratadine.

The salicylate is typically acetylsalicylic acid.

The present invention provides delivery systems which are combined in a highly reliable, easy to use and affordable manufacture that give the resulting dosage form unique characteristics to deliver single or multiple APIs regardless of physical-chemical compatibility and/or stability liabilities. The soft-gelatin delivery system can be filled with hydrophilic or lipophilic media to suspend various IR and/or MR dosage forms in drug solutions or plain liquid phases.

The delivery system of the invention is a viable alternative to the manufacturing of IR plus MR combinations in tablets and hard-gelatin capsules while enhancing dosing accuracy and by-passing dissolution barriers and coating issues. It also solves compatibility and stability issues for multivitamins, cold remedies, nutraceuticals and multiple other OTC medications. The invention also allows the formulation of combination products, highly needed to assure patient compliance and allow synergistic clinical effects in a safe and stable dosage form.

The invention also allows for ease of identification by color coding the shell, fill and/or contents minimizing counterfeiting risks.

The contents of my non-provisional applications filed Jul. 18, 2011, and concurrently filed with this application and based on provisional application Nos. 61/344,417 and 61/344,416 are incorporated by reference in their entirety as if they were individually denoted.

All patents, patent applications and publications cited in this application including all cited references in those applications and publications, are hereby incorporated by reference in their entirety for all purposes to the same extent as if each individual patent, patent application or publication were so individually denoted.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting.

It is to be understood that the terms used herein are merely descriptive rather than limiting and that various changes, numerous equivalents may be made without departing from the spirit or scope of the claimed invention.

The invention claimed is:

1. A dispensing and feeding device for dispensing and feeding solid dosage forms into a softgel capsule, said dispensing and feeding device including a hopper having said solid dosage forms, channelguides for transporting said solid dosage forms, and a grasping claw for dispensing said solid dosage forms, each grasping claw having volume capacity for grasping a fixed dose of the solid dosage forms coming through one of the said channelguide and configured for releasing the fixed dose into a pocket of the softgel.

2. A method for making softgel capsules having incorporated therein other solid dosage forms, said method comprising:
    (a) casting a gel-forming composition to make films;
    (b) passing said films through a pair of rotary dies having vacuum means to make pockets of a softgel capsule;
    (c) feeding via channelguides smaller solid dosage forms into said pockets using a lateral dispensing and feeding system that uses grasping claws, each grasping claw having volume capacity for grasping a fixed dose of the solid dosage forms coming through one of said channelguides and configured for releasing the fixed dose into a pocket of the softgel capsule;
    (d) filling said pockets with a medicine formulation in liquid form via a wedge segment; and
    (e) forming said softgel capsule by sealing the pockets together.

3. A process for making a softgel capsule having incorporated therein one or more smaller capsules, said method comprising:
    (a) feeding film sheets between a first die roll and a second die roll wherein each of the die rolls have capsule pockets in a plurality of rows and said capsule pockets have at least one orifice for application of suction;
    (b) applying suction while said film sheets are in place in the capsule pockets;
    (c) feeding preformed one or more smaller capsules onto the film sheets overlying the die rolls at positions having the capsule pockets via channelguides through a lateral dispensing device having a hopper and grasping claws, each grasping claw having volume capacity for grasping a fixed dose of the preformed smaller capsule coming through one of said channelguides and configured for releasing the fixed dose into a capsule pocket;
    (d) filling said capsule pockets also via a wedge segment with a liquid medical formulation; and
    (e) cutting the film sheets about the capsule pockets to form said softgel capsules having the one or more smaller capsules in combination with the liquid medical formulation.

* * * * *